United States Patent
Stahmann et al.

(10) Patent No.: US 8,784,310 B2
(45) Date of Patent: Jul. 22, 2014

(54) VASCULAR PRESSURE SENSOR WITH ELECTROCARDIOGRAM ELECTRODES

(75) Inventors: Jeffrey E. Stahmann, Ramsey, MN (US); Thomas W. Piaget, St. Paul, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 422 days.

(21) Appl. No.: 12/786,159

(22) Filed: May 24, 2010

(65) Prior Publication Data

US 2011/0004075 A1    Jan. 6, 2011

Related U.S. Application Data

(60) Provisional application No. 61/222,592, filed on Jul. 2, 2009.

(51) Int. Cl.
| | |
|---|---|
| A61B 5/02 | (2006.01) |
| A61B 5/0215 | (2006.01) |
| A61B 5/00 | (2006.01) |
| A61B 5/042 | (2006.01) |

(52) U.S. Cl.
CPC ............ *A61B 5/0215* (2013.01); *A61B 5/6846* (2013.01); *A61B 5/042* (2013.01)
USPC ........................................................ 600/301

(58) Field of Classification Search
USPC ................. 600/485, 486; 607/40, 9
See application file for complete search history.

(56) References Cited

U.S. PATENT DOCUMENTS

| | | | |
|---|---|---|---|
| 6,024,704 A * | 2/2000 | Meador et al. ............... | 600/486 |
| 6,296,615 B1 | 10/2001 | Brockway et al. | |
| 7,024,248 B2 | 4/2006 | Penner et al. | |
| 7,149,587 B2 | 12/2006 | Wardle et al. | |
| 7,218,966 B2 | 5/2007 | Haefner | |
| 7,803,121 B2 * | 9/2010 | Plouf et al. ................... | 600/486 |
| 2002/0065472 A1 | 5/2002 | Brockway et al. | |
| 2004/0106849 A1 | 6/2004 | Cho et al. | |
| 2004/0167410 A1 * | 8/2004 | Hettrick ....................... | 600/486 |
| 2005/0149132 A1 | 7/2005 | Libbus | |
| 2005/0154321 A1 * | 7/2005 | Wolinsky et al. ............ | 600/486 |

(Continued)

FOREIGN PATENT DOCUMENTS

| | | |
|---|---|---|
| EP | 1488735 | 12/2004 |
| WO | 0197687 | 12/2001 |

OTHER PUBLICATIONS

International Search Report and Written Opinion issued in PCT/US2010/035965, mailed Sep. 20, 2010, 16 pages.

*Primary Examiner* — Carl H Layno
*Assistant Examiner* — Jon Eric C Morales
(74) *Attorney, Agent, or Firm* — Faegre Baker Daniels LLP

(57) ABSTRACT

Devices, systems, and methods for sensing cardiac electrical activity and blood pressure within a blood vessel are disclosed. A vascular sensor includes a fixation element configured to secure the vascular sensor within a blood vessel, a sensor module housing coupled to the fixation element, a pressure sensor disposed within an interior portion of the housing and configured to sense blood pressure within the vessel, and a number of electrocardiogram sensing electrodes exposed to tissue and blood within the blood vessel and configured to sense cardiac electrical data within the blood vessel. A controller module processes the sensed cardiac electrical data and blood pressure data and stores the data within a memory unit and/or transmits the data to a communicating device in wireless communication with the vascular sensor.

15 Claims, 8 Drawing Sheets

(56) References Cited

U.S. PATENT DOCUMENTS

| | | |
|---|---|---|
| 2005/0288722 A1* | 12/2005 | Eigler et al. ............... 607/9 |
| 2006/0074453 A1 | 4/2006 | Kieval et al. |
| 2007/0043298 A1* | 2/2007 | Plouf et al. ............... 600/485 |
| 2007/0167984 A1 | 7/2007 | Kieval et al. |
| 2007/0293896 A1 | 12/2007 | Haefner |
| 2008/0177156 A1 | 7/2008 | Zhang et al. |
| 2008/0312712 A1* | 12/2008 | Penner ............... 607/40 |
| 2009/0281399 A1 | 11/2009 | Keel et al. |
| 2010/0114244 A1* | 5/2010 | Manda et al. ............... 607/60 |
| 2010/0197994 A1 | 8/2010 | Mehmanesh |

* cited by examiner

VASCULAR PRESSURE SENSOR WITH ELECTROCARDIOGRAM ELECTRODES

CROSS-REFERENCE TO RELATED APPLICATIONS

This application claims benefit under 35 U.S.C. §119 to U.S. Provisional Application No. 61/222,592, filed Jul. 2, 2009, entitled "Vascular Pressure Sensor With Electrocardiogram Electrodes," which is incorporated herein by reference in its entirety for all purposes.

TECHNICAL FIELD

The present invention relates generally to implantable medical devices for sensing multiple physiologic parameters within the body. More specifically, the present invention pertains to vascular pressure sensors that include electrocardiogram electrodes for sensing electrical activity within the heart, and to systems and methods of sensing blood pressure and cardiac electrical activity within the vasculature.

BACKGROUND

Implantable medical devices (IMDs) are utilized in a variety of medical applications for sensing and deriving physiologic parameters within the body. In cardiac rhythm management (CRM) systems used to monitor the status of a patient's heart, for example, an implantable sensor may sense various hemodynamic parameters within the atria and/or ventricles of the heart, or within the vessels leading into or from the heart. In one such system, for example, a remote pressure sensor implanted within one of the pulmonary arteries can be used to sense arterial blood pressure data.

The sensed hemodynamic data obtained from such devices can be used to derive information such as heart rate, cardiac output, and stroke volume. In some systems, the sensed hemodynamic data can be wirelessly transmitted to another implant within the body and/or to an external device for further analysis, often in conjunction with other sensed parameters. An example device adapted to sense arterial pressure measurements within a pulmonary artery and acoustically communicate those measurements to another implant or to an external device is described in U.S. Pat. No. 7,024,248, entitled "Systems and Methods For Communicating With Implantable Devices," the contents of which are incorporated herein by reference in its entirety for all purposes.

The interpretation and analysis of sensed blood pressure data may be difficult in some circumstances without correlating the data with the patient's cardiac rhythm. In diagnosing events or conditions such as arrhythmia or pulsus alternans, for example, it may be necessary to correlate the rhythm associated with the sensed blood pressure data with electrical activity occurring within the heart in order to accurately interpret the blood pressure data and diagnose the presence of the event or condition.

SUMMARY

The invention relates generally to implantable medical devices for sensing multiple physiologic parameters within the body, and in particular, vascular pressure sensors that include electrocardiogram electrodes for sensing electrical activity within the heart.

In Example 1, an illustrative implantable vascular sensor includes at least one fixation element configured to secure the vascular sensor within a blood vessel, a sensor module housing coupled to the fixation element, a pressure sensor disposed within an interior portion of the sensor module housing, the pressure sensor configured to sense blood pressure data within the blood vessel, a plurality of electrocardiogram sensing electrodes coupled to an exterior portion of the sensor, the sensing electrodes configured to sense cardiac electrical data within the blood vessel, and circuitry means for processing the cardiac electrical data and blood pressure data sensed by the electrocardiogram sensing electrodes and pressure sensor.

In Example 2, the vascular sensor of Example 1, wherein the plurality of electrocardiogram sensing electrodes includes a first sensing electrode coupled to a first exterior portion of the sensor module housing, and a second sensing electrode coupled to a second exterior portion of the sensor module housing spaced apart from the first exterior portion and electrically isolated from the first sensing electrode.

In Example 3, the vascular sensor of any of Examples 1-2, wherein the sensor module housing includes a sensor housing coupled to a power supply housing, the power supply housing containing an energy storage device.

In Example 4, the vascular sensor of Example 3, wherein the plurality of electrocardiogram sensing electrodes includes a first sensing electrode coupled to the at least one fixation element, and a second sensing electrode coupled to either the sensor housing or the power supply housing.

In Example 5, the vascular sensor of Example 3, wherein the plurality of sensing electrodes includes a first sensing electrode coupled to an exterior portion of the sensor housing, a second sensing electrode coupled to an exterior portion of the power supply housing.

In Example 6, the vascular sensor of Example 3, wherein the plurality of sensing electrodes includes a first sensing electrode coupled to a first side of the sensor housing, and a second sensing electrode coupled to a second side of the sensor housing opposite the first side.

In Example 7, the vascular sensor of Example 3, wherein the plurality of sensing electrodes includes a first sensing electrode coupled to an end of the sensor housing, and a second sensing electrode coupled to an end of the power supply housing.

In Example 8, the vascular sensor of any of Examples 1-7, wherein the at least one fixation element includes a first fixation element and a second fixation element, the first fixation element electrically coupled to a first sensing electrode, the second fixation element electrically coupled to a second sensing electrode.

In Example 9, the vascular sensor of any of Examples 1-8, further including a communication module configured to wirelessly transmit sensed cardiac electrical data and blood pressure data to a communicating device.

In Example 10, the vascular sensor of any of Examples 1-9, wherein the plurality of electrocardiogram sensing electrodes are conductive-type electrodes.

In Example 11, the vascular sensor of any of Examples 1-10, wherein the plurality of electrocardiogram sensing electrodes are capacitive-type electrodes.

In Example 12, the vascular sensor of any of Examples 1-11, wherein the circuitry means includes a controller module configured to generate an electrocardiogram waveform from cardiac electrical data sensed by the electrocardiogram sensing electrodes, and generate a pressure waveform from blood pressure data sensed by the pressure sensor.

In Example 13, the vascular sensor of Example 12, wherein the controller module is configured to associate the electrocardiogram waveform with the pressure waveform to detect an event or condition within the body.

In Example 14, a system for sensing cardiac electrical activity and blood pressure within a blood vessel, the system comprising an implantable vascular sensor, comprising a fixation element, a sensor module housing coupled to the expandable fixation element, a pressure sensor disposed within an interior portion of the sensor module housing, the pressure sensor configured to sense blood pressure within the blood vessel. The system further includes a plurality of electrocardiogram sensing electrodes coupled to an exterior portion of the sensor module housing and exposed to tissue within the blood vessel, the electrocardiogram sensing electrodes configured to sense cardiac electrical data within the blood vessel; circuitry for processing cardiac electrical data and blood pressure data sensed by the electrocardiogram sensing electrodes and pressure sensor; and a communication module configured to wirelessly transmit sensed cardiac electrical data and blood pressure data. The system further includes a communicating device configured to wirelessly receive the sensed cardiac electrical data and blood pressure data from the vascular sensor.

In Example 15, the system of Example 14, wherein the plurality of electrocardiogram sensing electrodes includes a first sensing electrode coupled to the exterior of the sensor module housing and a second sensing electrode coupled to the exterior of the sensor module housing and electrically insulated from the first sensing electrode.

In Example 16, the system of any of Examples 14-15, wherein the communication module includes an ultrasonic transducer, and wherein the ultrasonic transducer is configured to acoustically transmit sensed cardiac electrical data and blood pressure data to the communicating device.

In Example 17, the system of any of Examples 14-16, wherein at least one of the vascular sensor and communicating device is configured to generate an electrocardiogram waveform from the cardiac electrical sensed by the electrocardiogram sensing electrodes, and generate a pressure waveform from the blood pressure data sensed by the pressure sensor.

In Example 18, the system of Example 17, wherein the communicating device comprises an external monitor configured to display the electrocardiogram waveform and the pressure waveform.

In Example 19, a method of sensing cardiac electrical activity and blood pressure within a blood vessel, comprising implanting a vascular sensor within a blood vessel of a patient, the vascular sensor including a pressure sensor and a plurality of electrocardiogram sensing electrodes exposed to tissue within the blood vessel; sensing blood pressure data within the blood vessel using the pressure sensor; sensing cardiac electrical data within the blood vessel using the electrocardiogram sensing electrodes; wirelessly transmitting sensed blood pressure data and cardiac electrical data to a device in wireless communication with the vascular sensor; and analyzing the sensed blood pressure data and cardiac electrical data.

In Example 20, the method of Example 19, wherein analyzing the sensed blood pressure data and cardiac electrical data includes generating a pressure waveform from the sensed blood pressure data, generating an electrocardiogram waveform from the sensed cardiac electrical data, and associating the electrocardiogram waveform with the pressure waveform to detect an event or condition within the body.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
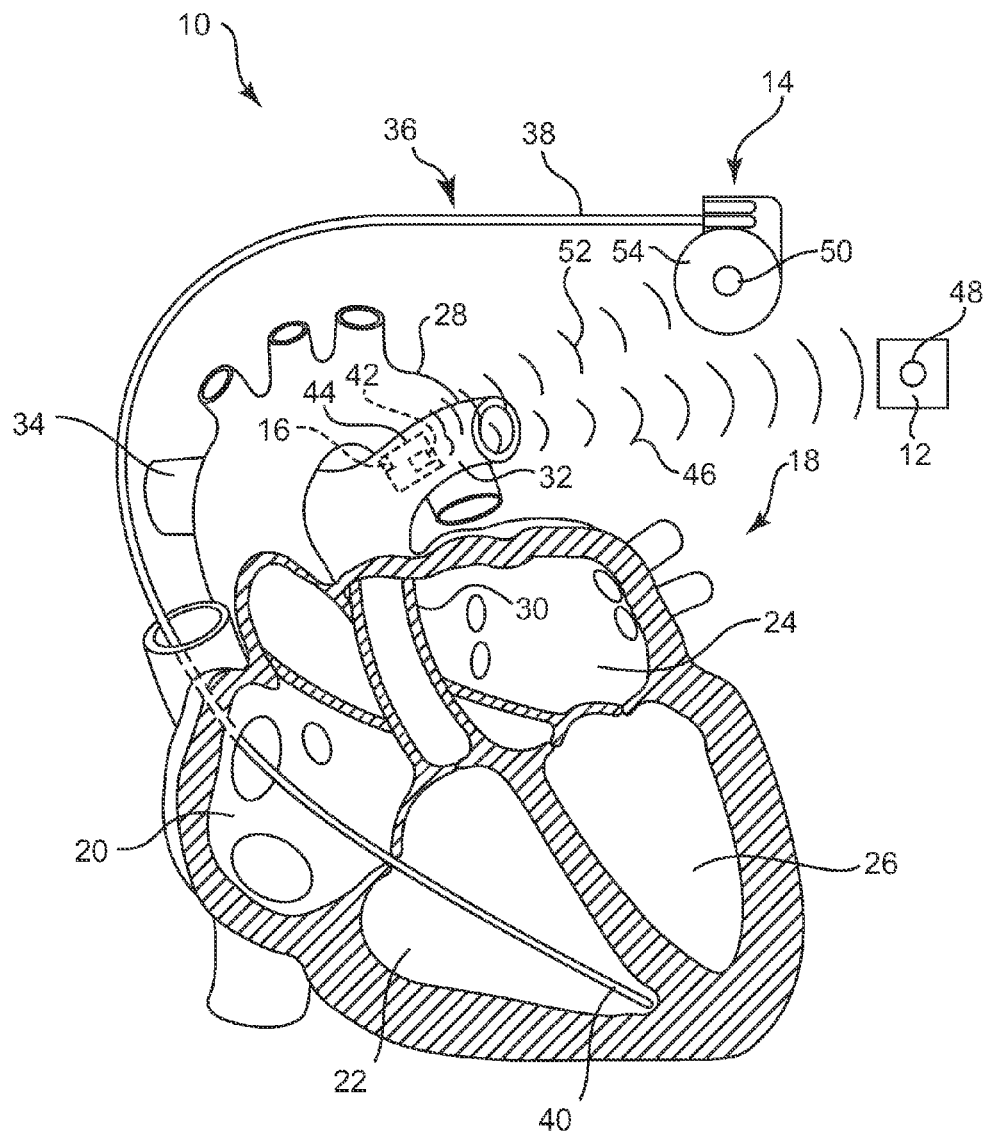
FIG. 1 is a schematic view of an illustrative cardiac rhythm management system employing an implantable medical device located within the body of a patient.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a schematic view of an illustrative system 10 employing an implantable medical device (IMD) located within the body of a patient. The system 10, illustratively a cardiac rhythm management system for providing cardiac rhythm management to a patient, includes an external monitor 12 (e.g., an external wand or programmer), a pulse generator 14 implanted within the body, and at least one remote IMD 16 implanted deeply within the patient's body such as in one of the pulmonary arteries leading from the heart 18, or in one of the atria or ventricles of the patient's heart 18. The heart 18 includes a right atrium 20, a right ventricle 22, a left atrium 24, a left ventricle 26, and an aorta 28. The right ventricle 22 leads to the main pulmonary artery 30 and the branches 32,34 of the main pulmonary artery 30.

In the illustrative system 10 shown, the pulse generator 14 is coupled to a lead 36 inserted into the patient's heart 18. The pulse generator 14 can be implanted subcutaneously within the body, typically at a location such as in the patient's chest or abdomen, although other implantation locations are possible. A proximal portion 38 of the lead 36 can be coupled to or formed integrally with the pulse generator 14. A distal portion 40 of the lead 36, in turn, can be implanted at a desired location within the heart 18 such as the right ventricle 22, as shown. Although the illustrative system 10 depicts only a single lead 36 inserted into the patient's heart 18, in other embodiments the system 10 may include multiple leads so as to electrically stimulate other areas of the heart 18. In some embodiments, for example, the distal portion of a second lead (not shown) may be implanted in the right atrium 20. In addition, or in lieu, another lead may be implanted in the left side of the heart 18 (e.g., in the coronary veins) to stimulate the left side of the heart 18. Other types of leads such as epicardial leads may also be utilized in addition to, or in lieu of, the lead 36 depicted in FIG. 1.

During operation, the lead 36 is configured to convey electrical signals between the heart 18 and the pulse generator 14. For example, in those embodiments where the pulse generator 14 is a pacemaker, the lead 36 can be utilized to deliver electrical therapeutic stimulus for pacing the heart 18. In those embodiments where the pulse generator 14 is an implantable cardioverter-defibrillator (ICD), the lead 36 can be utilized to deliver electric shocks to the heart 18 in response to an event such as ventricular fibrillation. In some embodiments, the pulse generator 14 includes both pacing and defibrillation capabilities.

The IMD 16 can be configured to perform one or more designated functions, including the sensing of one or more physiologic parameters within the body. In the embodiment of FIG. 1, the remote IMD 16 comprises a vascular pressure sensor implanted at a location deep within the body such as in the main pulmonary artery 30 or a branch 32,34 of the main pulmonary artery 30 (e.g., in the right or left pulmonary artery). An example of a vascular pressure sensor suitable for use in sensing intracardiac blood pressure is described in U.S. Pat. No. 6,764,446, entitled "Implantable Pressure Sensors and Methods for Making and Using Them," the contents of which are incorporated herein by reference in its entirety for all purposes.

The IMD 16 may be implanted in other regions of the patient's vasculature, in other body lumens, or in other areas of the body, and may comprise any type of chronically implanted device adapted to deliver therapy and/or monitor biological and chemical parameters, properties, and functions. The IMD 16 can be tasked, either alone or with other implanted or external devices, to provide various therapies within the body. In certain embodiments, for example, the IMD 16 can be used to aid in the prediction of heart decompensation of a heart failure patient and/or to aid in optimizing pacing and/or defibrillation therapy via the pulse generator 14 by taking intracardiac pressure measurements within the body. In some embodiments, and as discussed further herein, the intracardiac pressure measurements can be utilized either alone or in conjunction with electrocardiogram data sensed by the IMD 16 to aid in diagnosing various cardiac conditions or events such as arrhythmias, hypertension, and ischemia. Although a single IMD 16 is shown in FIG. 1, multiple such devices could be implanted at various locations within the body for sensing or monitoring physiologic parameters and/or providing therapy at multiple regions within the body.

In some embodiments, an acoustic communication link is used to wirelessly communicate between the IMD 16 and the external monitor 12, between the IMD 16 and the pulse generator 14, and/or between the IMD 16 and one or more other devices located inside or outside of the body. In the illustrative system 10 of FIG. 1, for example, an ultrasonic transducer 42 disposed within the housing 44 of the IMD 16 is configured to transmit an ultrasound signal 46 that can be received by the external monitor 12 and/or the pulse generator 14. An example ultrasonic transducer suitable for use with the IMD 16 for transmitting and receiving ultrasound signals is described in U.S. Pat. No. 6,140,740, entitled "Piezoelectric Transducer," the contents of which are incorporated herein by reference in its entirety for all purposes.

The external monitor 12 includes one or more ultrasonic transducers 48 configured to receive the ultrasound signal 46 and establish an acoustic communication link between the IMD 16 and the external monitor 12. In some embodiments, for example, the acoustic communication link between the remote IMD 16 and the external monitor 12 can be used to wirelessly transmit sensor data, operational status information, as well as other information from the IMD 16 to the external monitor 12. An example acoustic telemetry system employing ultrasonic transducers is described in U.S. Pat. No. 7,024,248, entitled "Systems and Methods For Communicating With Implantable Devices," the contents of which are incorporated herein by reference in its entirety for all purposes.

In some embodiments, the ultrasonic transducer(s) 48 for the external monitor 12 may transmit an ultrasound signal to the IMD 16 to prompt the IMD 16 to perform a desired operation. In one embodiment, for example, the external monitor 12 may transmit an acoustic wake-up command to the IMD 16, causing the IMD 16 to activate from an initial, low-power state for conserving power to an active, energized state for taking one or more sensor measurements and transmitting sensor data to the external monitor 12, to the pulse generator 14, and/or to another device located inside or outside of the body. In some embodiments, the external monitor 12 may transmit a command that prompts the IMD 16 to wake up only a portion of the IMD 16 and transmit one or more ultrasonic pulses without activating the sensor circuitry within the IMD 16.

While the system 10 of FIG. 1 includes an IMD 16 that communicates with an external monitor 12, in other embodiments the remote IMD 16 communicates with other devices located inside or outside of the patient's body. As further shown in FIG. 1, for example, the IMD 16 may be in acoustic communication with the pulse generator 14, which can include one or more ultrasonic transducers 50 adapted to receive an ultrasound signal 52 transmitted by the IMD 16. In certain embodiments, the ultrasonic transducer(s) 50 are coupled to an interior portion of the can 54 that encloses the various components of the pulse generator 14. In other embodiments, the ultrasonic transducer(s) 50 are located outside of the can 54, on a header of the can 54, or are coupled to the pulse generator 14 through a feedthrough provided on the can 54.

Although the system 10 depicted in FIG. 1 shows an acoustic link between the remote IMD 16 and the external monitor 12, and/or between the IMD 16 and the pulse generator 14, in other embodiments an acoustic link can be established between the remote IMD 16 and another device implanted within the body. In some embodiments, for example, an acoustic link can be established between a primary IMD 16 and one or more secondary IMDs 16 implanted within the body.

Figure 2:
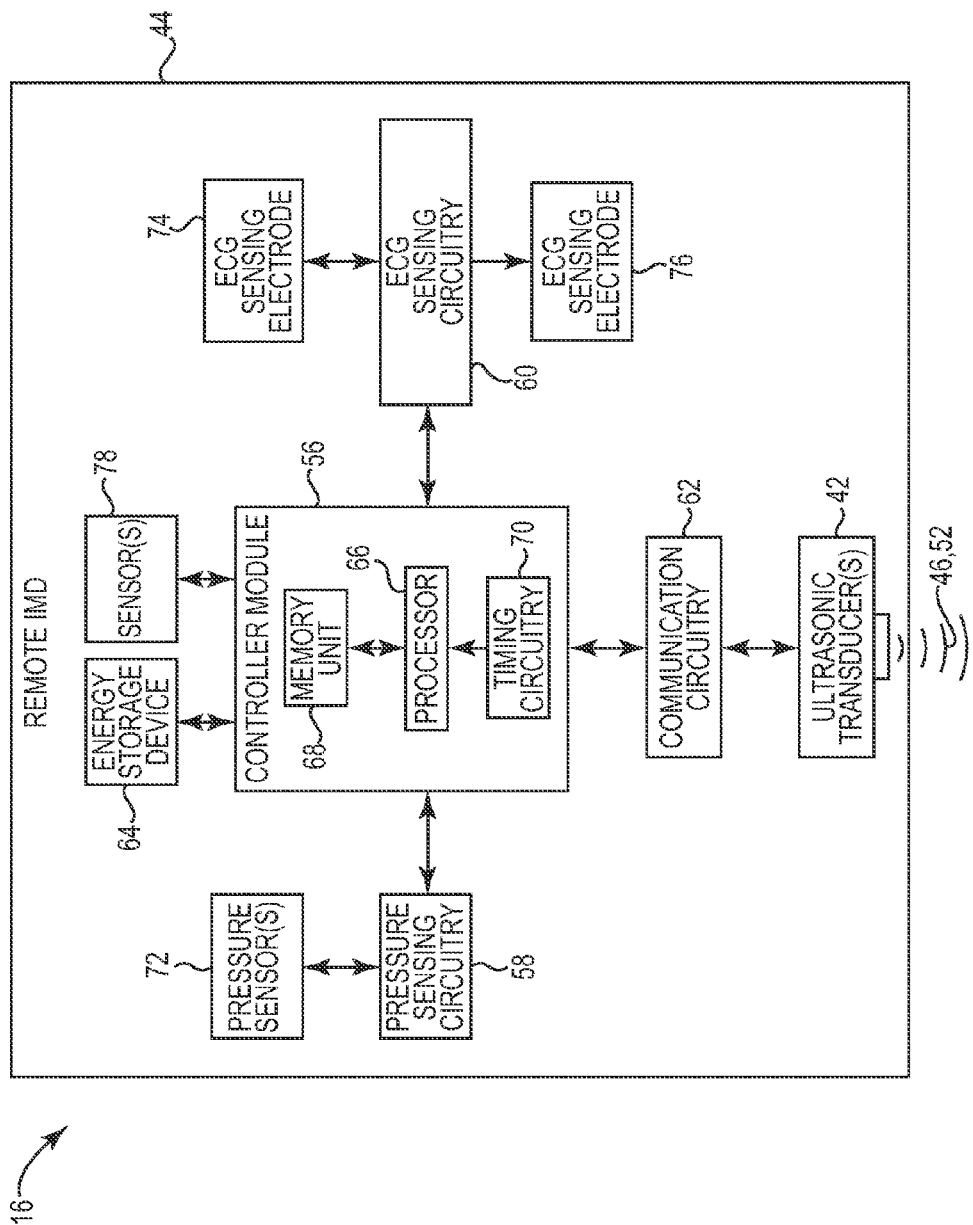
FIG. 2 is a block diagram showing several illustrative components of the implantable medical device of FIG. 1.

FIG. 2 is a block diagram showing several illustrative components of the IMD 16 of FIG. 1. As shown in FIG. 2, the IMD 16 includes a controller module 56 adapted to control the various operations and functions of the IMD 16, including pressure sensing circuitry 58 used for sensing intracardiac pressure sensing data, electrocardiogram sensing circuitry 60 for sensing cardiac electrical activity within the heart 18, and communication circuitry 62 for communicating sensed pressure data and sensed cardiac electrical activity from the IMD 16 to another device such as the external monitor 12 and/or pulse generator 14. An energy storage device 64 such as a battery or power capacitor is used to provide power to the various components of the remote IMD 16, including the controller module 56, the pressure and ECG sensing circuitry 58,60, and the communication circuitry 62.

The controller module 56 includes a processor 66 such as a microprocessor or microcontroller coupled to a memory unit 68 that includes operating instructions and/or software for the IMD 16. The memory unit 68 can include volatile memory and nonvolatile memory. In some embodiments, nonvolatile memory can store calibration data and parameter data. The volatile memory can include diagnostic and/or microprocessor-executable code, operating parameters, status data, and/or other data.

The controller module 56 also includes an oscillator or other timing circuitry 70 which directs the timing of activities to be performed by the IMD 16 once awoken from its low-power or sleep state. For example, the timing circuitry 70 can be used for timing the physiologic measurements taken by the IMD 16 and to generate timing markers to be associated with those measurements. The timing circuitry 70 may also be used for modulating the ultrasound signal(s) 46,52 transmitted by the ultrasonic transducer 42.

The controller module 56, including the processor 66, can be configured as a digital signal processor (DSP), a field programmable gate array (FPGA), an application specific integrated circuit (ASIC)-compatible device, and/or any other hardware component or software module for processing, analyzing, storing data, and controlling the operation of the IMD 16. Processor 66 executes instructions stored in the memory unit 68 or in other components or modules that may be present. In general, processor 66 executes instructions that cause the processor 66 to control or facilitate the functions of the IMD 16 and/or components of the IMD 16.

A pressure sensor 72 disposed within the housing 44 of the IMD 16 and coupled to the pressure sensing circuitry 58 is configured to measure intracardiac blood pressure data at the implantation site of the IMD 16. When implanted within a pulmonary artery, for example, the pressure sensor 72 and associated sensing circuitry 58 can be used to sense arterial blood pressure data at the implantation site. The sensed arterial blood pressure data can be transmitted in real-time to the external monitor 12 and/or pulse generator 14, or can be associated with timing markers and stored in the memory unit 68 for later transmission to the external monitor 12 and/or pulse generator 14.

A number of ECG sensing electrodes 74,76 coupled to the exterior of the IMD housing 44 and exposed to tissue within the pulmonary artery are configured to measure cardiac electrical activity within the body at the implantation site. Electrical activity produced by heart 18 results in a potential difference across the ECG sensing electrodes 74,76. ECG sensing circuitry 60 filters and amplifies the potential difference across the ECG sensing electrodes 74,76 and communicates this value to controller module 56. When implanted within a pulmonary artery, for example, the ECG sensing electrodes 74,76 can be configured to sense the presence and signature characteristics of the electrical impulses (P wave, QRS complex, T wave, etc.) as a result of the body's cardiac rhythm. From these sensed characteristics, the processor 66 determines the timing and magnitude of the cardiac electrical impulses of the heart 18 and generates an electrocardiogram waveform. The electrocardiogram waveform can be transmitted in real-time to the external monitor 12 and/or pulse generator 14, or can be associated with timing markers and stored in the memory unit 66 for later transmission to the external monitor 12 and/or pulse generator 14. In some embodiments, the external monitor 12 can be configured to display both the blood pressure waveform and the electrocardiogram waveform.

In some embodiments, the electrocardiogram waveform data generated by sensing cardiac electrical activity via the ECG sensing electrodes 74,76 can be used alone, or in conjunction with the sensed blood pressure measurements, to detect the presence of a cardiac condition or event occurring within the body. The electrocardiogram waveform data can also be used to regulate the delivery of electrical stimulus energy provided to the body via the pulse generator 14.

The IMD 16 may include other sensors 78 configured to sense other physiologic parameters within the body. Examples of other sensors 78 may include, but are not limited to, temperature, position, strain, pH, blood flow, posture, radiation level, and glucose level. In one embodiment, for example, a temperature sensor within the IMD 16 can sense temperature at the implantation site for calibrating the blood pressure measurements obtained from the pressure sensor 72.

The communication circuitry 62 enables wireless communication between the IMD 16 and the external monitor 12, the pulse generator 14, and/or other communicating device. In some embodiments, the ultrasonic transducer 42 for the IMD 16 may include one or more piezoelectric transducer elements configured to transmit and receive ultrasound signals. In a reception mode of operation, the ultrasonic transducer 42 can be configured to receive a control signal transmitted from the external monitor 12 and/or the pulse generator 14, which is fed to the controller module 56 when the remote IMD 16 is in the active state. In a transmit mode of operation, the ultrasonic transducer 42, or another ultrasonic transducer coupled to the IMD 16, is configured to transmit an ultrasound signal 46,52 to the external monitor 12, to the pulse generator 14, and/or to another device located inside or outside of the body. The transmitted ultrasound signal 46,52 can include sensor data obtained from the pressure sensor 72 and ECG sensing electrodes 74,76, information relating to the status or operation of the IMD 16 (e.g., power status, communication mode status, error correction information, etc.), as well as other information relating to the operation of the IMD 16. Although the IMD 16 of FIG. 2 includes an ultrasonic transducer 42 for acoustically communicating sensed data and/or other information to another device, in other embodiments other modes of wireless communication (e.g., RF, inductive, optical, etc.) may be utilized to communicate such data and information.

Figure 3:
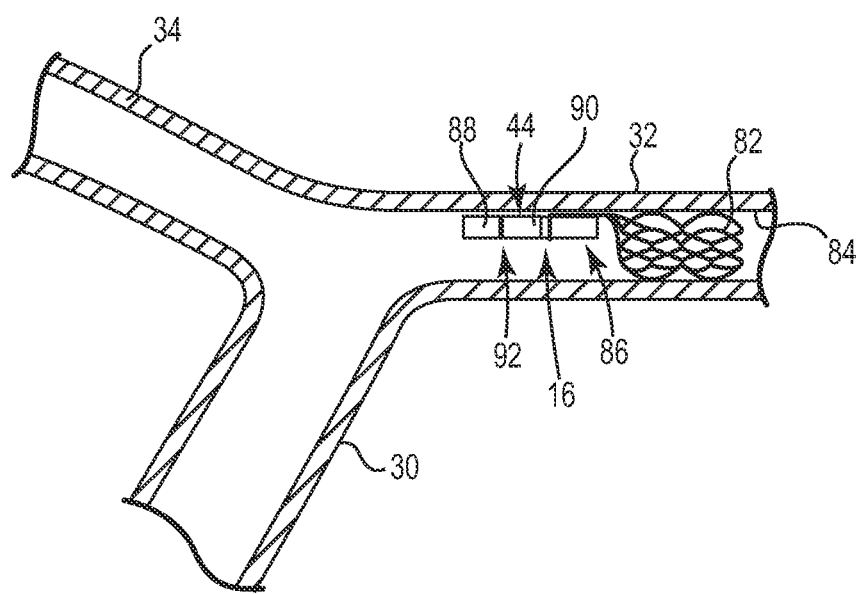
FIG. 3 is a schematic view showing the implantable medical device of FIG. 1 implanted within a pulmonary artery.

FIG. 3 is a schematic view showing the IMD 16 of FIG. 1 implanted within a pulmonary artery 32. As shown in FIG. 3, the IMD 16 includes a sensor housing 44 coupled to an expandable fixation element 82 which, when removed from within the interior of a delivery catheter or sheath (not shown), is configured to radially expand from a collapsed position to an expanded position within the artery 32. In a generally expanded position shown in FIG. 3, the fixation element 82 frictionally engages the interior wall 84 of the artery 32, securing the remote IMD 16 at a desired location within the artery 32. In some embodiments, the fixation element 82 comprises an electrically conductive material, and serves as part of an ECG sensing electrode for sensing cardiac electrical activity from within the artery 32.

The sensor housing 44 contains the various components of the IMD 16, including the controller module 56, the pressure sensor 72 and pressure sensing circuitry 58, the ultrasonic transducer 42 and communication circuitry 62, and the internal sensor(s) 78 described with respect to FIG. 2. In some embodiments, as shown in FIG. 3, the sensor housing 44 is coupled to a power supply housing 86 that contains the energy storage device 64 used to power the IMD 16.

A number of ECG sensing electrodes 88,90 coupled to the exterior of the sensor housing 44 are exposed to body tissue within the artery 32, and can be utilized (e.g., via the ECG sensing circuitry 60) for sensing changes in electrical activity occurring in the artery 32. A first ECG sensing electrode 88 coupled to an exterior portion of the sensor housing 44, for example, is configured to sense a first electrical parameter in the tissue adjacent to the electrode 88. A second ECG sensing electrode 90 coupled to the exterior of the housing 44 and to the power supply housing 86, in turn, is configured to sense a second electrical parameter in the tissue adjacent to the electrode 90. The second ECG sensing electrode 90 is electrically isolated from the first ECG sensing electrode 88 via an insulative break 92 on the sensor housing 44. The electrical activity produced by the heart 18 is detected at ECG sensing electrodes 88,90 as an electric potential, which can be detected by the ECG sensing circuitry 60 within the IMD 16.

The sensed changes in electrical activity can then be analyzed by the processor 66 to detect the presence and signature characteristics of the electrical impulses occurring over each cardiac cycle. For example, the change in electrical activity sensed by the ECG sensing electrodes 88,90 can be analyzed to detect the P wave, PR interval, QRS complex, ST segment, QT interval, and T wave signature components of the ECG complex. From these sensed characteristics, the IMD 16 determines the timing and magnitude of the cardiac electrical impulses and generates an electrocardiogram waveform.

In some embodiments, the ECG waveform data can be used in conjunction with the sensed blood pressure data obtained by the pressure sensor(s) 72 and associated pressure sensing circuitry 58 to correlate the timing of the blood pressure measurements with the timing of the cardiac cycle. In certain embodiments, for example, the ECG waveform data obtained from the ECG sensing electrodes 88,90 can be used to interpret the rhythm of the pressure waveform obtained via the pressure sensor 72, and in particular, correlating the timing of various events in the pressure waveform with the electrical activity of the heart. This correlation can then be used to aid in identifying and diagnosing various events or cardiac conditions including, but not limited to, detecting arrhythmias such as atrial fibrillation, ventricular fibrillation, conditions such as pulsus alternans, or detecting the occurrence of a single event such as a myocardial infarction. Since the same timer is used in the sensing of pressure and ECG measurements, the resultant pressure waveform and ECG waveform are inherently aligned in time with each other. As a result, no time compensation steps are necessary to align the data.

Figure 4:
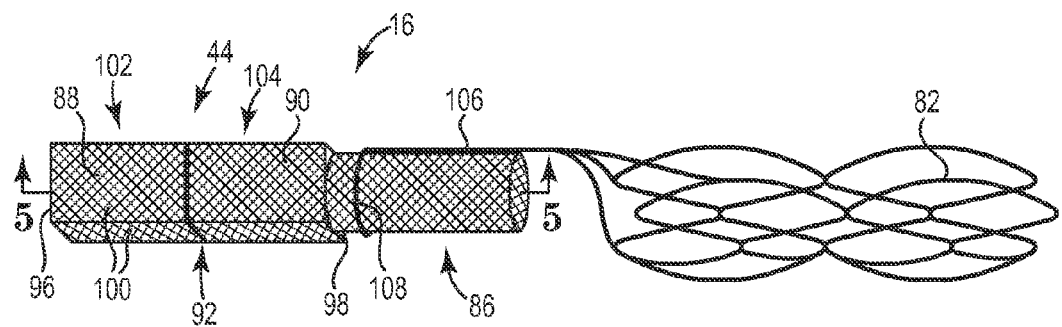
FIG. 4 is a perspective view of the implantable medical device of FIG. 1, showing an illustrative embodiment of the ECG sensing electrodes.

FIG. 4 is a perspective view of the IMD 16 of FIG. 3, showing an illustrative embodiment of the ECG sensing electrodes 86,88 in greater detail. As shown in FIG. 4, the sensor housing 44 has a substantially rectangular shape including a first end 96, a second end 98, and a number of sides 100. The second end 98 of the sensor housing 44 is coupled to the power supply housing 86, and includes an electrical feedthrough (not shown) that electrically connects the energy storage device 64 within the housing 86 to the controller module 56.

In some embodiments, the first ECG sensing electrode 88 comprises a layer or coating of electrically conductive material disposed over the first end 96 and a proximal portion 102 of each of the sides 100 extending from the first end 96 to the insulating break 92. The second ECG sensing electrode 90, in turn, comprises a layer or coating of electrically conductive material disposed over a distal portion 104 of each of the sides 100, extending from the insulating break 92 to the second end 98. Examples of conductive materials that can be used in fabricating the ECG sensing electrodes 88,90 can include, but are not limited to, gold, platinum, or tantalum. Other electrically conductive materials are also possible. In some embodiments, the ECG sensing electrodes 88,90 are conductive-type electrodes that directly measure electrical activity produced by the heart 18, which can be fed via as a DC signal to the ECG sensing circuitry 60 within the IMD 16.

In the embodiment of FIG. 4, the ECG sensing electrodes 88,90 are disposed adjacent to the exterior of the sensor housing 44 along each of the sides 100, which serves to increase the active surface area exposed to the presence of blood and tissue within the vasculature for sensing cardiac electrical activity. In other embodiments, the first and second ECG electrodes 88,90 are disposed adjacent to only select sides 100 of the sensor housing 44, or may be provided on only the ends 96,98 of the housing 44.

In certain embodiments, and as further shown in FIG. 4, the second ECG sensing electrode 90 may further extend about all or a portion of the exterior of the power module housing 86, allowing the housing 86 to also serve as part of the electrode 90. A tether wire 106 extending proximally from the fixation element 82 is connected to the power module housing 86 via a conductive ring 108, which electrically connects the second ECG sensing electrode 90 to the fixation element 82. Due to the electrical coupling of the fixation element 82 to the second sensing electrode 90, the fixation element 82 also senses cardiac electrical activity at the implantation site.

Figure 5:
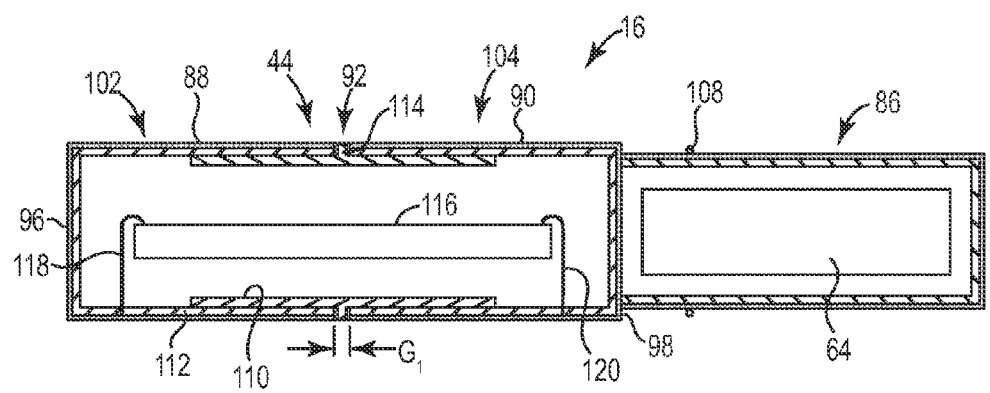
FIG. 5 is a partial cross-sectional view showing the sensor housing and power supply housing along line 5-5 in FIG. 4.

An electrically insulative break 92 located on each of the sides 100 of the sensor housing 44 electrically isolates the first ECG sensing electrode 88 from the second ECG sensing electrode 90. As further shown in FIG. 5, which is a partial cross-sectional view of the sensor housing 44 and power supply housing 86 along line 5-5 in FIG. 4, the insulative break 92 comprises an annular, non-conductive member 110 disposed adjacent to an exterior, titanium wall 112 of the sensor housing 44. A portion 114 of the non-conductive member 110 protruding outwardly through the exterior wall 112 provides an electrically insulative gap $G_1$ between the ECG sensing electrodes 88,90, which serves to isolate the ECG sensing electrodes 88,90 from each other, and which further serves to insulate the interior components within the sensor housing 44 from the surrounding blood and tissue within the vasculature. Each of the ECG sensing electrodes 88,90 are connected to a circuit board 116 within the sensor housing 44 via a respective wire lead 118,120, which electrically connects the electrodes 88,90 to the ECG sensing circuitry 60 discussed above with respect to FIG. 3. Other internal connectors (not shown) may also be used to electrically connect other components to the circuit board 116.

Figure 6:
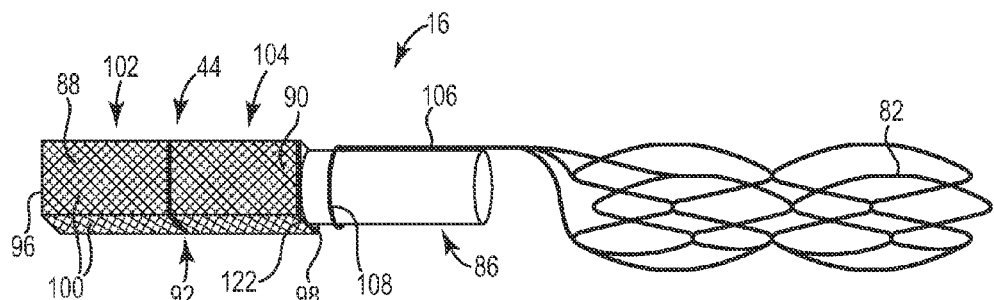
FIG. 6 is a perspective view of the implantable medical device of FIG. 1, showing another illustrative embodiment of the ECG sensing electrodes.

FIG. 6 is a perspective view of the IMD 16 of FIG. 1, showing another illustrative embodiment of the ECG sensing electrodes 88,90. In the embodiment of FIG. 6, the first ECG sensing electrode 88 comprises a layer or coating of electrically conductive material disposed over the first end 96 and a proximal portion 102 of each of the sides 100. The second ECG sensing electrode 90, in turn, comprises a layer or coating of electrically conductive material disposed over only a distal portion 104 of each of the sides 100, extending from the insulative break 92 to the second end 98 of the sensor housing 44. A second insulative break 122 on the second end 98 of the sensor housing 44 electrically insulates the second ECG sensing electrode 90 from the power supply housing 86. In such configuration, the power supply housing 86 and fixation element 82 do not serve as part of the second ECG sensing electrode 90.

Figure 7:
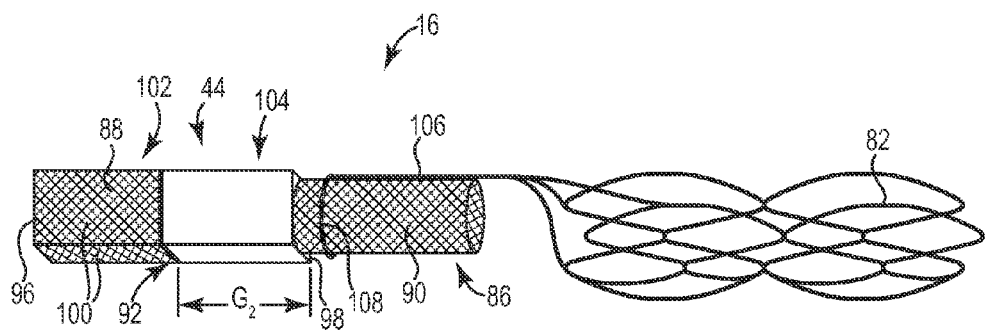
FIG. 7 is a perspective view of the implantable medical device of FIG. 1, showing another illustrative embodiment of the ECG sensing electrodes.

FIG. 7 is a perspective view of the IMD 16 of FIG. 1, showing another illustrative embodiment of the ECG sensing electrodes 88,90. In the embodiment of FIG. 7, the first ECG sensing electrode 88 comprises a layer or coating of electrically conductive material disposed over the first end 96 and the proximal portion 102 of each of the sides 100 of the sensor housing 44. The second ECG sensing electrode 90, in turn, comprises a layer or coating of electrically conductive material disposed over only the power supply housing 86. The distal portion 104 of each of the sides 100 does not include an active sensing electrode surface, thus forming a gap or spacing $G_2$ between the first ECG sensing electrode 88 and the second ECG sensing electrode 90. In use, this gap or spacing $G_2$ between the ECG sensing electrodes 88,90 increases the ability to sense slight changes in potential difference between the electrodes 88,90.

Figure 8:
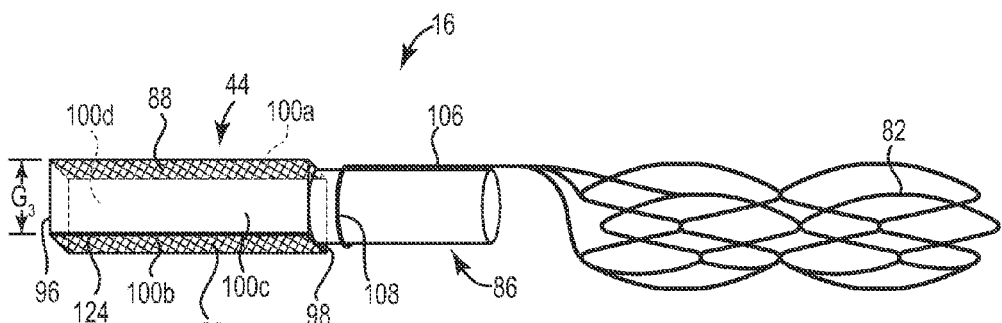
FIG. 8 is a perspective view of the implantable medical device of FIG. 1, showing another illustrative embodiment of the ECG sensing electrodes.

FIG. 8 is a perspective view of the IMD 16 of FIG. 1, showing another illustrative embodiment of the ECG sensing electrodes 88,90. In the embodiment of FIG. 8, the first ECG sensing electrode 88 comprises a layer or coating of electrically conductive material disposed over all or a portion of a first side 100a of the sensor housing 44. The second ECG sensing electrode 90, in turn, comprises a layer or coating of electrically conductive material disposed over all or a portion of a second side 100b of the sensor housing 44 opposite of the first side 100a. An insulative break 124 disposed between the second ECG sensing electrode 90 and the exterior surface of the sensor housing 44 electrically isolates the second ECG sensing electrode 90 from the first ECG sensing electrode 88, the second housing 44, and the power supply housing 86. The sides 100c,100d contiguous to each of the ECG sensing electrodes 88,90 do not include an active electrode surface, thus forming a gap or spacing $G_3$ between the first ECG sensing electrode 88 and the second ECG sensing electrode 90, as shown. In use, this gap or spacing $G_3$ between the ECG sensing electrodes 88,90 increases the ability to sense slight changes in potential difference between the electrodes 88,90.

Although the ECG sensing electrodes 88,90 are disposed on opposing sides 100a,100b of the sensor housing 44, in other embodiments the electrodes 88,90 may be arranged such that the electrodes 88,90 are disposed on contiguous sides of the sensor housing 44. For example, the first ECG sensing electrode 88 may be located on a first side 100a of the sensor housing 44 whereas the second ECG sensing electrode 90 may be disposed on a second side 100c of the housing 44 contiguous to the first side 100a. Other configurations are also possible.

Figure 9A:
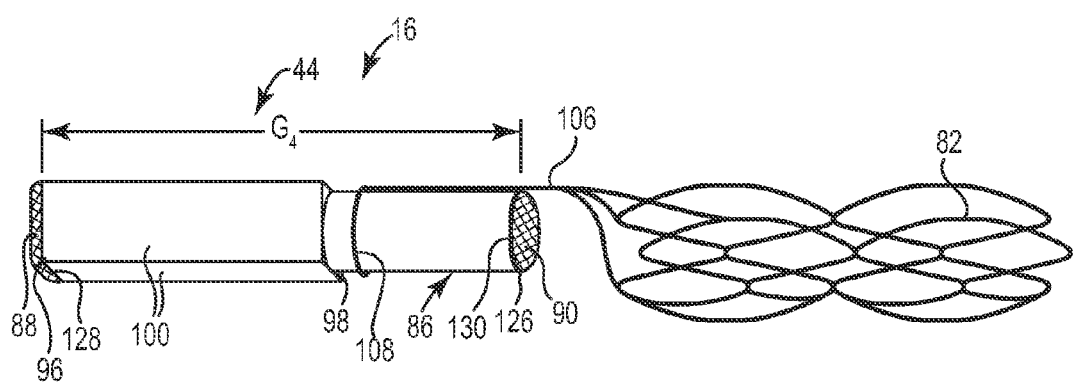
FIG. 9a is a perspective view of the implantable medical device of FIG. 1, showing another illustrative embodiment of the ECG sensing electrodes.

FIG. 9a is a perspective view of the IMD 16 of FIG. 1, showing another illustrative embodiment of the ECG sensing electrodes 88,90. In the embodiment of FIG. 9a, the first ECG sensing electrode 88 comprises a layer or coating of electrically conductive material disposed over an end 96 of the sensor housing 44. The second ECG sensing electrode 90, in turn, comprises a layer or coating of electrically conductive material disposed over an end 126 of the power supply housing 86. A first insulative break 128 disposed between the first ECG sensing electrode 88 and the exterior surface of the sensor housing 44 at end 96 electrically isolates the first ECG sensing electrode 88 from the sensor housing 44, power supply housing 86, and the second ECG sensing electrode 90. A second insulative break 130 disposed between the second ECG sensing electrode 90 and the exterior surface of the power supply housing 86 at end 126 electrically insulates the second ECG sensing electrode 90 from the power supply housing 86, the sensor housing 44, and the first ECG sensing electrode 88. The sides 100 of the sensor housing 44 and a portion of the power supply housing 86 do not include active electrode surfaces, thus forming a gap or spacing $G_4$ between the ECG sensing electrodes 88,90, as shown. In use, this gap or spacing $G_4$ between the ECG sensing electrodes 88,90 increases the ability to sense slight changes in potential difference between the electrodes 88,90.

Figure 9B:
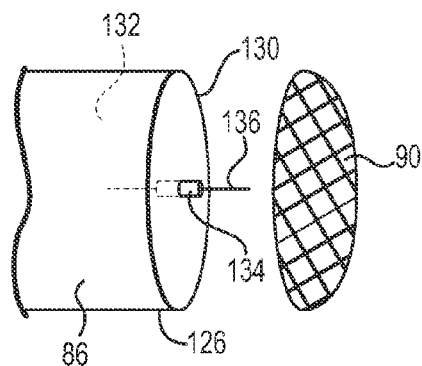
FIG. 9B is an assembly view showing the connection of an ECG sensing electrode to the power supply housing of FIG. 9A.

FIG. 9B is an assembly view showing the connection of the second ECG sensing electrode 90 to the end 126 of the power supply housing. As further shown in FIG. 9B, and in some embodiments, the second ECG sensing electrode 90 has a rounded or domical shape, and is electrically connected to the power supply housing 86 via an electrical feedthrough 134 that extends through the insulative break 130, end 126, and into the interior 132 of the power supply housing 86. A number of wires 136 connected to the sensing electrode 90 and extending through the electrical feedthrough 134 connect the electrode 90 to the ECG sensing circuitry 60 discussed herein with respect to FIG. 2. If desired, a similar feedthrough connection for connecting the first ECG sensing electrode 88 to the sensor housing 44 can also be utilized.

In some embodiments, the ECG sensing electrodes 88,90 each comprise conductive electrical sensors that sense changes in potential difference within the vasculature due to the electrical activity of the heart. Other types of sensing electrodes can also be employed to detect and sense cardiac electrical activity within the vasculature. Examples of other types of sensing electrodes can include, but are not limited to, capacitive, inductive, impedance, and magnetic-type sensing electrodes.

Figure 10:
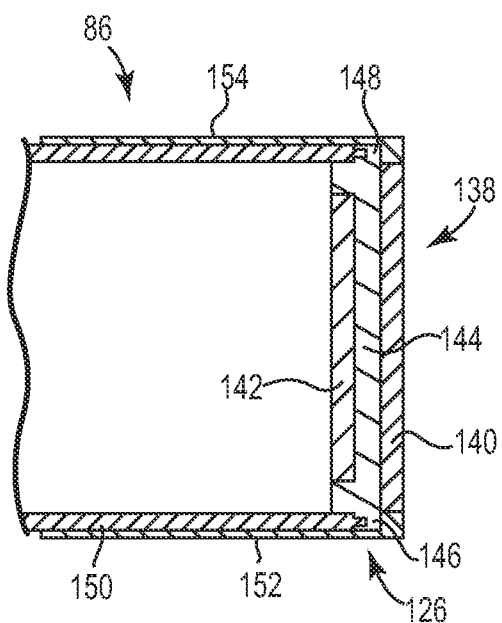
FIG. 10 is a partial cross-sectional view of a capacitive-type ECG sensing electrode in accordance with an illustrative embodiment.

FIG. 10 is a partial cross-sectional view showing a capacitive-type ECG sensing electrode 138 coupled to the power supply housing 86. As shown in FIG. 10, the ECG sensing electrode 138 includes a first capacitive plate 140 and second capacitive plate 142, each located at or near the end 126 of the power supply housing 86. The capacitive plates 142,144 each comprise an electrically conductive material, and are separated from each other via a dielectric layer 144, which connects at each end 146,148 to a wall 150 of the power supply housing 85. A layer or coating of insulation 152,154 disposed over the housing wall 150 at or near end 126 insulates the portion of the housing 86 adjacent to the sensing electrode 138.

Figure 11:
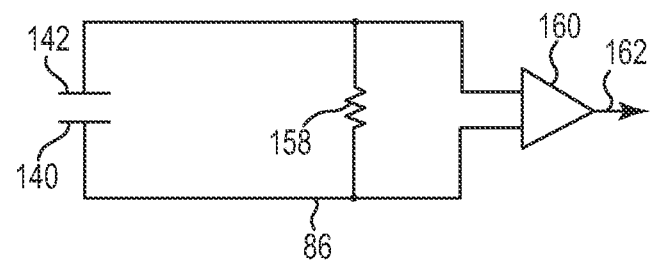
FIG. 11 is a an electrical schematic of the capacitive-type ECG sensing electrode of FIG. 10.

When implanted within a blood vessel, an outer surface 154 of the first capacitive plate 140 is exposed to blood and tissue within the surrounding vasculature, and is configured to sense an electric potential within the vessel due to the electrical activity of the heart. As further shown in the electrical schematic of FIG. 11, electrical energy produced by the heart results in a potential difference between the capacitive plate 140 and the conductive wall of the housing 86. The potential difference between capacitive plate 140 and housing 86 causes a current to flow in load resistor 158, the terminals of which are connected between the housing 86 and the capacitive plate 142. The terminals of load resistor 158 are also connected across the inputs to an amplifier 160. The potential difference between capacitive plate 140 and housing 86 causes current to flow in load resistor 158, producing a voltage across load resistor 158. This voltage is amplified by amplifier 160, which outputs a voltage signal 162 that can be used to generate an ECG waveform.

Figure 12:
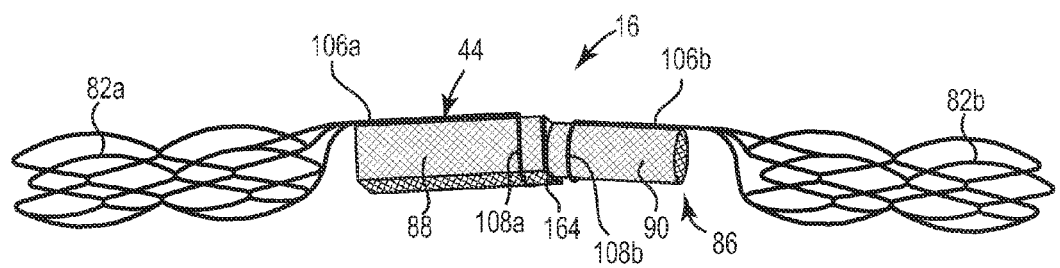
FIG. 12 is a perspective view showing another illustrative implantable medical device including a number of ECG sensing electrodes each coupled to a separate fixation element.

FIG. 12 is a perspective view of the IMD 16 of FIG. 1, showing another illustrative embodiment of the ECG sensing electrodes 88,90. In the embodiment of FIG. 12, the IMD 16 includes multiple fixation elements 82a,82b that can be expanded to secure the IMD 16 within a blood vessel. In some embodiments, the fixation elements 82a,82b can be used to secure the IMD 16 at multiple locations along the length of a blood vessel or in a network of blood vessels as discussed, for example, in U.S. Pat. No. 7,572,228, entitled "Devices For Fixing A Sensor In A Lumen," the contents of which are incorporated herein by reference in its entirety for all purposes. In some embodiments, and as further shown in FIG. 12, the sensor housing 44 may be articulated relative to the power supply housing 86 such that the fixation elements 82a,82b are longitudinally offset at a slight angle from each other. Such articulation, for example, may facilitate anchoring of the IMD 16 in tortuous vessels.

The first ECG sensing electrode 88 comprises a layer or coating of electrically conductive material disposed over all or a portion of the sensor housing 44. The second ECG sensing electrode 90, in turn, comprises a layer or coating of electrically conductive material disposed over all or a portion of the power supply housing 86. An insulative break 164 disposed between the sensor housing 44 and the power supply housing 86 electrically isolates the first ECG sensing electrode 88 from the second ECG sensing electrode 90.

The fixation elements 82a,82b may each be electrically connected to a respective ECG sensing electrode 88,90, allowing the elements 82a,82b to further serve as electrodes for sensing cardiac electrical activity within the vasculature. A first tether wire 106a extending from a first fixation element 82a, for example, is coupled to the exterior surface of the first ECG sensing electrode 88 via conductive ring 108a, thus electrically connecting the first ECG sensing electrode 88 to the fixation element 82a. A second connecting wire 106b extending from a second fixation element 82b, in turn, is coupled to the exterior surface of the second ECG sensing electrode 90 via conductive ring 108b, thus electrically connecting the second ECG sensing electrode 90 to the fixation element 82b. In such configuration, the fixation elements 82a,82b also serve to sense cardiac electrical activity within the vasculature.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed is:

1. A leadless implantable vascular sensor, comprising:
   at least one fixation element configured to secure the vascular sensor within a blood vessel;
   a sensor module housing coupled to the fixation element and including:
      a sensor housing including a plurality of exterior surfaces defining an interior portion of the sensor housing;
      a power supply housing coupled to the sensor housing and containing an energy storage device;
   a pressure sensor disposed within the interior portion of the sensor housing, the pressure sensor configured to sense blood pressure data within the blood vessel;
   a first electrocardiogram sensing electrode disposed on an exterior portion of the sensor housing;
   a second electrocardiogram sensing electrode disposed on an exterior portion of the power supply housing;
   an insulative break disposed on at least a portion of at least one of the plurality of exterior surfaces of the sensor housing and electrically isolating the first electrocardiogram sensing electrode from the second electrocardiogram sensing electrode,
   the sensor module housing further comprising a pair of parallel and opposed ends, the pair of parallel and opposed ends comprising a first end disposed on the sensor housing and a second end disposed on the power supply housing, and a plurality of sides disposed between the first end and the second end and including the plurality of exterior surfaces of the sensor housing, wherein:
      the first electrocardiogram sensing electrode is disposed on the first end; and
      the second electrocardiogram sensing electrode is disposed on the second end;
   the first and second electrocardiogram sensing electrodes configured to sense cardiac electrical data within the blood vessel; and
   circuitry means for processing the cardiac electrical data and blood pressure data sensed by the electrocardiogram sensing electrodes and pressure sensor to correlate the timing of the blood pressure data with a timing of a cardiac cycle.

2. The vascular sensor of claim 1, wherein:
   the first electrocardiogram sensing electrode is electrically connected to the at least one fixation element; and
   the second electrocardiogram sensing electrode is coupled to the sensor housing.

3. The vascular sensor of claim 2, further comprising:
   a tether wire extending proximally from the at least one fixation element; and
   a conductive ring disposed at a proximal end of the tether wire, wherein the conductive ring is coupled to the power supply housing, thereby electrically coupling the first electrocardiogram sensing electrode to the at least one fixation element.

4. The vascular sensor of claim 1, wherein the at least one fixation element includes a first fixation element and a second fixation element, the first fixation element electrically coupled to the first electrocardiogram sensing electrode, the second fixation element electrically coupled to the second electrocardiogram sensing electrode.

5. The vascular sensor of claim 1, further including a communication module configured to wirelessly transmit sensed cardiac electrical data and blood pressure data to a communicating device.

6. The vascular sensor of claim 1, wherein the first and second electrocardiogram sensing electrodes are conductive-type electrodes.

7. The vascular sensor of claim 1, wherein the first and second electrocardiogram sensing electrodes are capacitive-type electrodes.

8. The vascular sensor of claim 1, wherein the circuitry means includes a controller module configured to:
   generate an electrocardiogram waveform from cardiac electrical data sensed by the electrocardiogram sensing electrodes; and
   generate a pressure waveform from blood pressure data sensed by the pressure sensor.

9. The vascular sensor of claim 8, wherein the controller module is configured to associate the electrocardiogram waveform with the pressure waveform to detect an event or condition within the body.

10. The vascular sensor of claim 1, further comprising a sensor coupled to the circuitry means, the sensor being configured to sense at least one of position, blood flow, posture, radiation level, and glucose level.

11. A system for sensing cardiac electrical activity and blood pressure within a blood vessel, the system comprising:
a leadless implantable vascular sensor, comprising:
an expandable fixation element;
a sensor module housing coupled to the expandable fixation element and including:
a sensor housing including a plurality of exterior surfaces defining an interior portion of the sensor housing;
a power supply housing coupled to the sensor housing and containing an energy storage device;
a pressure sensor disposed within the interior portion of the sensor housing, the pressure sensor configured to sense blood pressure within the blood vessel;
a first electrocardiogram sensing electrode disposed on an exterior portion of the sensor housing;
a second electrocardiogram sensing electrode disposed on an exterior portion of the power supply housing;
an insulative break disposed on at least a portion of at least one of the plurality of exterior surfaces of the sensor housing and electrically isolating the first electrocardiogram sensing electrode from the second electrocardiogram sensing electrode;
the sensor module housing further comprising a pair of parallel and opposed ends, the pair of parallel and opposed ends comprising a first end disposed on the sensor housing and a second end disposed on the power supply housing, and a plurality of sides disposed between the first end and the second end and including the plurality of exterior surfaces of the sensor housing, wherein:
the first electrocardiogram sensing electrode is disposed on the first end; and
the second electrocardiogram sensing electrode is disposed on the second end;
wherein the first and second electrocardiogram sensing electrodes are exposed to tissue within the blood vessel and configured to sense cardiac electrical data within the blood vessel;
circuitry for processing cardiac electrical data and blood pressure data sensed by the electrocardiogram sensing electrodes and pressure sensor; and
a communication module configured to wirelessly transmit sensed cardiac electrical data and blood pressure data; and
a communicating device configured to wirelessly receive the sensed cardiac electrical data and blood pressure data from the vascular sensor.

12. The system of claim 11, wherein the communication module includes an ultrasonic transducer, and wherein the ultrasonic transducer is configured to acoustically transmit sensed cardiac electrical data and blood pressure data to the communicating device.

13. The system of claim 11, wherein at least one of the vascular sensor and communicating device is configured to:
generate an electrocardiogram waveform from the cardiac electrical sensed by the electrocardiogram sensing electrodes; and
generate a pressure waveform from the blood pressure data sensed by the pressure sensor.

14. The system of claim 13, wherein the communicating device comprises an external monitor configured to display the electrocardiogram waveform and the pressure waveform.

15. A method of sensing cardiac electrical activity and blood pressure within a blood vessel, comprising:
implanting a leadless vascular sensor within a blood vessel of a patient, the vascular sensor including:
a vascular sensor housing including:
a sensor housing including a plurality of exterior surfaces defining an interior portion of the sensor housing;
a power supply housing coupled to the sensor housing and containing an energy storage device;
a pressure sensor disposed within the interior portion of the sensor housing;
a first electrocardiogram sensing electrode disposed on an exterior portion of the sensor housing and exposed to tissue within the blood vessel;
a second electrocardiogram sensing electrode disposed on an exterior portion of the power supply housing and exposed to tissue within the blood vessel; and
an insulative break disposed on at least a portion of at least one of the plurality of exterior surfaces of the sensor housing and electrically isolating the first electrocardiogram sensing electrode from the second electrocardiogram sensing electrode;
the sensor module housing further comprising a pair of parallel and opposed ends, the pair of parallel and opposed ends comprising a first end disposed on the sensor housing and a second end disposed on the power supply housing, and a plurality of sides disposed between the first end and the second end and including the plurality of exterior surfaces of the sensor housing, wherein:
the first electrocardiogram sensing electrode is disposed on the first end; and
the second electrocardiogram sensing electrode is disposed on the second end;
sensing blood pressure data within the blood vessel using the pressure sensor;
sensing cardiac electrical data within the blood vessel using the first and second electrocardiogram sensing electrodes;
wirelessly transmitting sensed blood pressure data and cardiac electrical data to a device in wireless communication with the vascular sensor; and
analyzing the sensed blood pressure data and cardiac electrical data, wherein analyzing the sensed blood pressure data and cardiac electrical data includes:
generating a pressure waveform from the sensed blood pressure data;
generating an electrocardiogram waveform from the sensed cardiac electrical data; and
correlating the timing of one or more events in the blood pressure waveform with electrocardiogram waveform to detect an event or condition within the body.

* * * * *